(12) United States Patent
Cascone

(10) Patent No.: US 7,794,652 B2
(45) Date of Patent: Sep. 14, 2010

(54) NOBLE DENTAL ALLOY

(75) Inventor: Paul J. Cascone, Del Mar, CA (US)

(73) Assignee: The Argen Corporation, San Diego, CA (US)

( * ) Notice: Subject to any disclaimer, the term of this patent is extended or adjusted under 35 U.S.C. 154(b) by 565 days.

(21) Appl. No.: 11/298,085

(22) Filed: Dec. 8, 2005

(65) Prior Publication Data

US 2006/0147334 A1    Jul. 6, 2006

Related U.S. Application Data

(60) Provisional application No. 60/639,359, filed on Dec. 27, 2004.

(51) Int. Cl.
*C22C 19/07* (2006.01)
*C22C 5/04* (2006.01)
*C22C 30/00* (2006.01)
*C22C 5/00* (2006.01)

(52) U.S. Cl. ........................ 420/436; 420/462; 420/580; 420/588; 148/425; 148/430; 148/442

(58) Field of Classification Search ............... 420/8, 420/34, 35, 36, 82, 428, 435, 436, 437, 440, 420/441, 442, 444, 452, 456, 459, 461–468, 420/501–512, 580, 581, 583, 588, 433; 75/955; 148/400, 320, 325, 423, 425, 426, 427, 430, 148/442

See application file for complete search history.

(56) References Cited

U.S. PATENT DOCUMENTS

| 4,038,074 | A |   | 7/1977 | Davitz |
| 4,253,869 | A |   | 3/1981 | Prosen |
| 4,255,190 | A |   | 3/1981 | Prosen |
| 4,382,909 | A |   | 5/1983 | Zwingmann |
| 4,387,072 | A | * | 6/1983 | Schaffer .................. 420/463 |
| 4,459,263 | A |   | 7/1984 | Prasad |
| 6,554,920 | B1 |   | 4/2003 | Jackson et al. |
| 6,613,275 | B1 |   | 9/2003 | Vuilleme |
| 6,656,420 | B2 |   | 12/2003 | Prasad et al. |
| 6,756,012 | B2 |   | 6/2004 | Prasad |
| 2002/0041820 | A1 | * | 4/2002 | Prasad ..................... 420/437 |
| 2005/0158693 | A1 | * | 7/2005 | Prasad et al. ............. 433/207 |

FOREIGN PATENT DOCUMENTS

| DE | 1104195 |   | 4/1961 |
| DE | 101 36 997 A1 | * | 2/2003 |
| EP | 0 347 614 A1 |   | 12/1989 |
| FR | 2015889 |   | 4/1970 |
| FR | 2 733 416 A1 |   | 10/1996 |
| FR | 2 750 858 A1 |   | 1/1998 |
| FR | 2 750 867 A1 |   | 1/1998 |
| FR | 2750858 |   | 1/1998 |
| FR | 2750867 |   | 1/1998 |
| JP | 58-110633 | * | 7/1983 |
| JP | 58-110633 A |   | 7/1983 |
| JP | 60-135550 A |   | 7/1985 |
| WO | WO 03/011231 A1 |   | 2/2003 |

OTHER PUBLICATIONS

"Dental Alloy." Patent No. 58110633. Japan. (English Translation of JP 58-110633.).*
English translation of German Patent Publication number: DE 1104195; in the name of Deutsche Gold et al.; Date of publication Apr. 6, 1961.

* cited by examiner

*Primary Examiner*—Scott Kastler
*Assistant Examiner*—Vanessa Velasquez
(74) *Attorney, Agent, or Firm*—Kauth, Pomeroy, Peck & Bailey LLP

(57) ABSTRACT

A dental prosthesis may be cast and machined from a cobalt-, iron- and/or nickel-chromium base dental alloy comprising at least 25% metal selected from the group consisting of ruthenium, platinum, palladium, iridium, osmium, rhodium, and gold wherein the major portion or at least 15%, whichever is larger, of metal in this group is ruthenium; from 15 to 30% chromium; and a principal balance of metal selected from the group consisting of iron. nickel and cobalt.

9 Claims, No Drawings

NOBLE DENTAL ALLOY

CROSS-REFERENCE TO RELATED APPLICATION(S)

This application claims the benefit of the filing date of U.S. Provisional Application 60/639,359, filed Dec. 27, 2004.

FIELD OF THE INVENTION

This invention concerns an iron, cobalt and/or nickel based dental alloy containing at least 25% gold and/or platinum group elements with the principal portion of these noble metals being ruthenium.

BACKGROUND OF THE INVENTION

Dental alloys employed in the porcelain-fused-to-metal processing technique may be classified into several groups: gold based; palladium based; cobalt based and nickel based. The cost of the alloy is dependent upon the commodity prices of the alloy components. For example, as of December 2004, the cost of the major components of such alloys are: gold $442 per Troy ounce, palladium $183 per Troy ounce; cobalt $1 per Troy ounce; and nickel $0.3 per Troy ounce. The economic advantage of the base metals cobalt and nickel is obvious but the functional characteristics of the base metal alloys do not compare with those of the gold or palladium based dental products. In general, the base metal alloys are more difficult to cast, grind and bond to porcelain.

There have been numerous attempts to improve the functional characteristics of cobalt and nickel alloys through the addition of gold and the platinum group metals (the platinum group metals comprise platinum, palladium, rhodium, iridium, osmium and ruthenium).

Exemplary US patents describing such dental alloys:

| Patentee | U.S. patent | Comments |
| --- | --- | --- |
| Davitz | 4,038,074 | Describes a nickel chromium alloy that may have 1 to 5 wt. % palladium |
| Prosen | 4,253,869 | Describes a cobalt chromium alloy that may contain 7 to 15 wt. % ruthenium |
| Prosen | 4,255,190 | Describes a cobalt chromium alloy that may contain 1 to 5 wt. % ruthenium with gallium plus tungsten |
| Zwingmann | 4,382,909 | Describes a cobalt chromium alloy that may contain 1 to 70 wt. % palladium |
| Prasad | 4,459,263 | Describes a cobalt chromium alloy that may contain 5 to 15 wt. % ruthenium |
| Vuilleme | 6,613,275 | Describes a cobalt chromium alloy that may contain 0.5 to 4 wt. % gold |
| Prasad | 6,656,420 | Describes an alloy that may contain 25 to 60 wt. % gold and up to 2 wt. % ruthenium balance cobalt. |
| Prasad | 6,756,012 | Describes a cobalt chromium alloy that may contain up to 20 wt. % platinum or palladium, up to 10 wt. % gold and up to 6 wt. % ruthenium |

In each case, some improvement in the functional characteristics of the base metal alloy is achieved through the addition of gold and the platinum group metals. This invention expands the effort to improve the base metal based alloys through the judicious use of ruthenium additions in higher amounts than used in previous alloys.

BRIEF SUMMARY OF THE INVENTION

Thus, there is provided in practice of this invention according to a presently preferred embodiment, a dental alloy comprising from 15 to 30 wt % chromium and at least 25 wt % of metal selected from the group of ruthenium, platinum, palladium, iridium, osmium, rhodium and gold, provided that the major proportion of this group or over 15 wt %, whichever is greater, is ruthenium. The principal balance of the alloy is cobalt, nickel and/or iron.

DETAILED DESCRIPTION OF THE INVENTION

A noble dental alloy is considered to be one with at least 25% noble metal content, the noble metals comprising ruthenium, platinum, palladium, iridium, osmium, rhodium and gold. The alloy provided herein is noble, but is considered to be a cobalt, nickel and/or iron base alloy since a high proportion of these base metals are in the alloy. The alloy has more than 15% ruthenium (all percentages herein are by weight).

The choice of ruthenium has both metallurgical and economic benefits.

Considering the price of gold and the platinum group metals as of December 2004:

| Rhodium | $1,320 per Troy ounce |
| --- | --- |
| Platinum | 844 |
| Gold | 442 |
| Osmium | 400 |
| Palladium | 183 |
| Iridium | 170 |
| Ruthenium | 67 |

Ruthenium is by far the lowest costing element of the group so that is an economic advantage to maximize the ruthenium additions in place of gold and the other platinum group elements. The main reason for the low cost is that ruthenium is a by-product of producing the other platinum group elements but does not have many industrial uses.

From a metallurgical perspective, ruthenium substitutes for molybdenum, tungsten and to a certain extent chromium in both cobalt and nickel based alloys, and even iron based alloys which are, surprisingly, suitable for dental prosthesis applications. Ruthenium acts as an alloy strengthener, lowers the thermal expansion of the alloy (to better match thermal expansion of dental porcelains) and reduces the alloy's oxidation rate.

Alloys suitable for practice of this invention comprise at least 25% of metal selected from the group consisting of ruthenium, platinum, palladium, iridium, osmium, rhodium and gold, provided that the major proportion of this group or over 15%, whichever is greater, is ruthenium; from 15 to 30% chromium; up to 15% gallium; up to 5% silicon; up to 1% boron; up to 5% of metal selected from the group consisting of niobium, tantalum and rhenium; and a balance of metal selected from the group consisting of iron, cobalt and nickel. Mixtures of cobalt, nickel and iron, for example, may be used since from a metallurgical perspective they may be considered equivalents when the ruthenium content is so high. The lower chromium alloys are preferred since easier to cast and they produce less slag upon melting.

Thus, the alloy is a iron- nickel- and/or cobalt-chromium base alloy with a principal addition of ruthenium of more than 15%, and preferably at least 25%. If the ruthenium content of the alloy is less than 25%, other noble metals to bring the total to at least 25% may be used, provided that most of the noble metal is ruthenium. The amount of noble metal in the alloy may be more than 25% (provided that most of the noble metal is ruthenium) but there is no economic advantage to using higher amounts of costly material.

Both ruthenium and chromium protect the alloy from corrosion and oxidation. All of the iron alloys tested passed the ISO corrosion and cytotoxicity tests. This is surprising since iron is so easily dissolved in an acidic environment. The ruthenium apparently enobles the alloy, as opposed to the chromium that forms an oxide to protect the alloy from adverse reactions.

This alloy may be modified by addition of up to about 10% gallium, up to about 5% silicon or up to about 1% boron (or appropriate combinations of these elements) to enhance the casting characteristics of the alloy. Gallium, for example, lowers the melting temperature of the alloy so that it can be melted with a natural gas- or propane-oxygen torch commonly used in dental laboratories.

Up to about 5% of niobium, tantalum and/or rhenium may be added to the alloy for grain refinement. Finer grain castings are more readily ground to a smooth finish suitable for covering with dental ceramics. Interestingly, iron alloys are easier to grind and finish than similar alloys with cobalt.

An example of an alloy of this invention with ruthenium as the only noble metal comprises cobalt 40%, chromium 25%, ruthenium 25% and gallium 10%. This alloy is readily cast and processed using standard dental laboratory equipment and materials.

The physical properties of this exemplary alloy are:

| Ultimate Tensile Strength: | 115,000 psi |
|---|---|
| Yield Strength (0.2% offset) | 85,000 psi |
| Elongation | 5% |
| Modulus of elasticity | 30,000,000 psi |
| Vickers hardness | 440 |

The thermal expansion of the alloy was found to be $13.9 \times 10^{-6}/°C$ at 600° C. Several popular dental porcelains are successfully bonded to the alloy. and both single crowns and bridgework are readily fabricated with no special handling requirements beyond usual dental laboratory procedures.

This alloy was successfully processed in a pilot production batch of 15 pounds using standard foundry processing techniques for cobalt alloys. Biological testing found the alloy to be non-cytotoxic.

The ruthenium content of about 25 wt % eliminated the need for any addition of molybdenum or tungsten.

The gallium addition lowered the melting range so that the alloy was able to be cast with a gas-oxygen torch. Alternatively, small silicon and boron additions can also improve the alloy's ability to be cast. If the alloy is to be cast by induction heating then the melting range can be higher, reducing the need for gallium.

Despite the high hardness value the alloy was able to be ground using traditional dental laboratory grinding media. The alloy is especially suited for use with newer CAD/CAM applications where no casting is required. A block of the alloy is ground into the final prosthesis shape.

Other exemplary compositions made in practice of this invention include:

Cobalt 40%, chromium 25%, ruthenium 25%, gallium 10%.

Iron 50%, chromium 15%, ruthenium 25%, gallium 10%

Chromium 15-25%, ruthenium 25%, gallium 5-10%, and the balance iron.

A sinterable noble alloy may also be prepared comprising at least 25% noble metal including from 25 to 30% ruthenium, 5 to 10% chromium, 10 to 15% gallium and a balance selected from the group consisting of iron, nickel and cobalt, preferably primarily or entirely iron, and preferably without nickel. Such an alloy may also be used as a casting or as a blank for machining a dental prosthesis.

By reducing the chromium content below 10%, and preferably to about 7%, formation of surface oxides or slag that would interfere with sintering can be avoided. Appreciable amounts of readily oxidizable metals with stable high melting oxides, such as aluminum, should also be avoided.

Up to 5% silicon and/or up to 1% boron may be substituted for part of the gallium for lowering melting point of the alloy. Higher amounts of ruthenium than 30% may also be suitable with sufficient additions of gallium or other metals for maintaining an acceptable melting point.

The alloy may also comprise up to 5% of a metal selected from the group consisting of niobium, tantalum and rhenium for grain refining.

A suitable alloy without nickel may comprise more than 15% ruthenium, from 15 to 30% chromium and a balance of metal selected from the group consisting of cobalt and iron, and substantially free of aluminum.

What is claimed is:

1. A dental alloy comprising:
    at least 25 wt % of at least one metal selected from the group consisting of ruthenium, platinum, palladium, iridium, osmium, rhodium, and gold provided more than 15 wt % of the total dental alloy composition is ruthenium;
    15 to 30 wt % chromium;
    5 to 15 wt % gallium such that the alloy can be melted with a natural gas- or propane-oxygen torch; and
    at least 40 wt % of cobalt.

2. A dental alloy according to claim 1 further comprising up to 5 wt % silicon and/or up to 1 wt % boron.

3. A dental alloy according to claim 1 further comprising up to 5 wt % of a metal selected from the group consisting of niobium, tantalum and rhenium.

4. A dental prosthesis including an alloy comprising:
    at least 25 wt % of at least one metal selected from the group consisting of ruthenium, platinum, palladium, iridium, osmium, rhodium, and gold provided more than 15 wt % of the total dental alloy composition is ruthenium;
    from 15 to 30 wt % chromium;
    5 to 15 wt % gallium such that the alloy can be melted with a natural gas- or propane-oxygen torch; and
    at least 40 wt % of cobalt.

5. A dental prosthesis according to claim 4 further comprising up to 5 wt % silicon and/or up to 1 wt % boron.

6. A dental prosthesis according to claim 4 further comprising up to 5 wt % of a metal selected from the group consisting of niobium, tantalum and rhenium.

7. A blank for machining a dental prosthesis including an alloy comprising:
- at least 25 wt % of at least one metal selected from the group consisting of ruthenium, platinum, palladium, iridium, osmium, rhodium, and gold provided more than 15 wt % of the total dental alloy composition is ruthenium;
- from 15 to 30 wt % chromium;
- 5 to 15 wt % gallium such that the alloy can be melted with a natural gas- or propane-oxygen torch; and
- at least 40 wt % of cobalt.

8. A blank for machining a dental prosthesis according to claim 7 wherein the alloy further comprising up to 5 wt % silicon and/or up to 1 wt % boron.

9. A blank for machining a dental prosthesis according to claim 7 wherein the alloy further comprises up to 5 wt % of a metal selected from the group consisting of niobium, tantalum and rhenium.

* * * * *